United States Patent [19]

Hudson et al.

[11] Patent Number: 4,485,117
[45] Date of Patent: Nov. 27, 1984

[54] ANTIPROTOZOAL COMPOUNDS

[76] Inventors: Alan T. Hudson, Lustleigh, Stonehouse La., Halstead, Sevenoaks, Kent; Anthony W. Randall, 27 Hayes Garden, Hayes, Kent, both of England

[21] Appl. No.: 433,867

[22] Filed: Oct. 13, 1982

[30] Foreign Application Priority Data

Oct. 16, 1981 [GB] United Kingdom ............. 8131206

[51] Int. Cl.³ .................. A01N 9/24; C07C 50/12
[52] U.S. Cl. .................. 424/331; 260/396 R
[58] Field of Search .......... 260/396 R; 424/331, 424/251, 253, 258

[56] References Cited

U.S. PATENT DOCUMENTS

| | | | |
|---|---|---|---|
| 2,553,647 | 5/1951 | Fieser | 260/396 |
| 3,347,742 | 10/1967 | Rogers | 424/331 |
| 3,393,211 | 7/1968 | Fisher et al. | 260/396 |
| 3,578,686 | 5/1971 | Tullar et al. | 424/331 |
| 3,602,991 | 8/1972 | Tullar et al. | 424/331 |
| 4,110,473 | 8/1978 | Fugitt et al. | 424/331 |

Primary Examiner—Glennon H. Hollrah
Assistant Examiner—Raymond Covington
Attorney, Agent, or Firm—Donald Brown

[57] ABSTRACT 1,4-Naphthoquinones of formula (I), methods for their preparation, pharmaceutical and veterinary formulations thereof and the use thereof in human and animal therapy are disclosed.

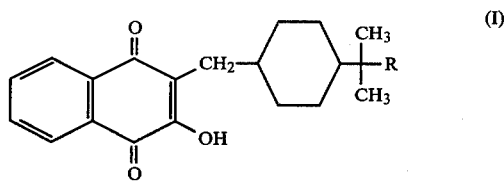

Particularly preferred compounds of formula (I) are 2-(4'-t-butylcyclohexyl)-3-hydroxy-1,4-naphthoquinone and 2-hydroxy-3-(4'-t-pentylcyclohexyl)-1,4-naphthoquinone. The compounds are of value as antiprotozoal agents, in particular antimalarial and anticoccidial agents.

21 Claims, No Drawings

ANTIPROTOZOAL COMPOUNDS

The present invention relates to naphthoquinones and their use in chemotherapy. More specifically the invention is concerned with certain 2-substituted-3-hydroxy-1,4-naphthoquinones, the preparation thereof, formulations thereof and the use thereof in the chemotherapy of human and animal protozoal infections.

2-Substituted-3-hydroxy-1,4-naphthoquinones have previously been described in the art as possessing antiprotozoal activity, in particular antimalarial and, to a lesser extent, anticoccidial activity. Thus Fieser et al. (*J. Amer. Chem. Soc.* 1948, 70, 3156) disclosed some hundreds of such compounds as possessing antimalarial activity. A number of these, in which a cycloalkyl group was attached to the quinone nucleus, were considered particularly active and were described in U.S. Pat. No. 2,553,648. A number of compounds were administered to man, but the compounds administered suffered from the disadvantage that large doses were required for therapeutic effect in man. Subsequently attention shifted to compounds having an w-cyclohexyl alkyl side chain, in particular menoctone, 2-(8-cyclohexyloctyl)-3-hydroxy-1,4-naphthoquinone (eg. Fieser et. al. *J.Med. Chem.* 1967,10, 513) but again interest waned because of poor activity in man.

U.S. Pat. No. 3,347,742 taught the use of 2-(4'-cyclohexylcyclohexyl)-1,4-naphthoquinone as an anticoccidial agent but this compound has never been commercialised.

It has now surprisingly been found that certain substituted naphthoquinones exhibit a much higher activity against the human parasite *Plasmodium falciparum* than related compounds previously considered as candidate antimalarial agents. In addition the compounds exhibit good, broad spectrum activity against commercially important Eimeria species, the causative organisms of coccidiosis.

The invention accordingly provides, in a first aspect, compounds of the formula (I)

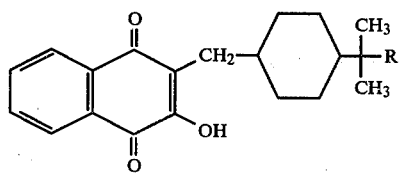

(I)

in which R is an alkyl group of from 1 to 10 carbon atoms, and pharmaceutically acceptable salts thereof.

European Patent Application No. 78,101,426 refers, inter alia, to 3-hydroxy-1,4-naphthoquinones in which the substituent in the 2-position is a $C_{3-12}$ cycloalkyl ring optionally bearing as a substituent a $C_{1-4}$ alkyl group, in particular a methyl group. However no specific compounds bearing a substituent are disclosed, nor is there any indication of which positions of the cycloalkyl ring are to be substituted.

It should be noted that in the unsubstituted 1,4-naphthoquinone ring the 2 and 3 positions are identical and thus, in the naming of the compounds, convention will indicate whether the cyclohexyl substituent or the hydroxyl group is in the 2 position. For convenience throughout this specification when the compounds are referred to non-specifically the substituent is defined as in the 2 position.

In the compounds of formula (I) R suitably is a straight chain $C_{1-4}$ alkyl group. Preferred groups are methyl and ethyl.

It will be appreciated that the compounds of formula (I) may exist as cis or trans isomers, that is to say that the cyclohexyl ring may be cis or trans substituted by the naphthoquinone nucleus and the 4-t-alkyl group. The invention includes both cis and trans isomers and mixtures thereof in any ratio. In general when the compound is in the form of a mixture of isomers the trans isomer will be present in an amount of about 50% or will be the predominant isomer but mixtures in which the cis isomer predominates are also included within the scope of the invention. The specific ratio of isomers may be varied as required; typical mixtures include those in which the cis/trans isomer ratio is about 1:1, 40:60 and 5:95.

Specific compounds included within the scope of formula (I) include:
2-(4'-t-butylcyclohexyl)-3-hydroxy-1,4-naphthoquinone; and 2-hydroxy-3-(4'-t-pentylcyclohexyl)-1,4-naphthoquinone; including pure cis and pure trans isomers and mixtures thereof.

The compounds of formula (I) may exist in a tautomeric form in which the hydroxyl group donates its proton to one of the oxo groups, and such tautomeric forms are included within the scope of this invention. However it is believed that the form shown in formula (I) is the stable form.

Since the hydroxyl group in the compounds of formula (I) may form salts with appropriate bases, pharmaceutically acceptable salts include those formed with an alkali metal cation, such as sodium or potassium, and those with organic bases such as ethanolamine, diethanolamine and N-methyl glucamine.

The compounds of formula (I) may be prepared by any method known in the art for the preparation of compounds of analogous structure.

One such method involves converting the corresponding 3-halogeno-, eg. 3-chloro- or 3-bromo, analogues of formula (II) in which X is halogen into the 3-hydroxy-substituted compounds by alkaline hydrolysis, for example with an alkali metal hydroxide in a suitable medium. For instance potassium hydroxide in aqueous methanolic medium has been found convenient.

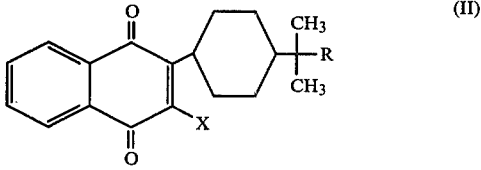

(II)

The compounds of formula (II) above are novel compounds and thus provide a further aspect of the invention. The compounds of formula (II) may be prepared by methods known in the art for the preparation of compounds of analogous structure, for example the method described by Fieser, L., *J. Am. Chem. Soc.*, 1948,3165 et seq.

The compounds according to formula (I) may also be prepared from the corresponding 2-hydroxy-3-(4'-t-alkylcyclohexylmethyl)-1,4-naphthoquinone of formula (III) by Hooker oxidation (c.f. for example *J. Am. Chem. Soc.,* 1948, 3174 or 3215):

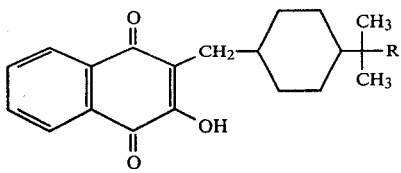

wherein R is as hereinbefore defined.

The compounds of formula (III) are themselves also novel compounds. The compounds of formula (III) may be prepared by methods known for the preparation of compounds of analogous structure to the method described by Fieser in *J. Am. Chem. Soc.,* 1948, 3165 eg. by reaction of a 2-halo-1,4-naphthoquinone with the appropriate (4-t-alkyl cyclohexyl) acetic acid.

A further method for the preparation of compounds of formula (I) comprises conversion of a compound of formula (V) by methods known in the art:

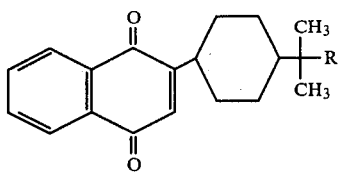

where R is as defined hereinabove

For example the compound of formula (V) may be halogenated (eg brominated) to provide compounds of formula (II) herein which may then be hydrolysed to compounds of formula (I). Alternatively the compounds of formula (V) may be epoxidised to provide a compound of formula (VI)

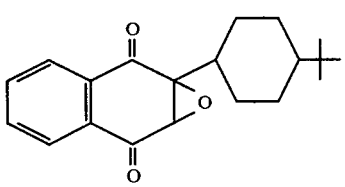

which may then be hydrolysed to a compound of formula (I) for example with dilute aqueous acid or dilute aqueous base.

The compound of formula (V) may also be subjected to a Thiele acetylation by reaction with an appropriate acetylating agent (eg acetic anhydride) in the presence of an oxidising agent (eg perchloric acid) to provide compounds of formula (VIIa). Compounds of formula (VIIa) may be converted to compounds of formula (VIIb) by hydrolysis which compounds may be converted to compounds of formula (I) by oxidation eg. by a method analogous to that described in Organic Reactions, vol 19 p222. Suitable oxidising agents include, for example, ferric chloride and a mineral acid or chromic acid.

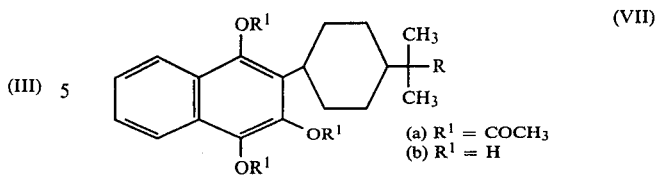

It will be appreciated to those skilled in the art that the processes described above may lead either to isomeric mixtures (cis and trans) of the compounds of formula (I), or, where an isomerically pure starting material is employed, to pure cis or trans compound of formula (I). In this respect the compounds of formula (III) are particularly valuable where it is desired that a pure cis or trans isomer be prepared.

A further method for the preparation of compounds of formula (I) comprises reacting a compound of formula (IV)

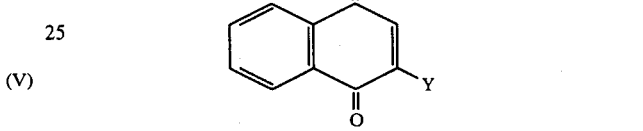

wherein Y is a halogeno (eg. chloro or bromo) atom or a hydroxy, acetoxy or $C_{1-6}$ alkoxy group with a cyclohexyl donor compound containing the moiety

where R is as hereinbefore defined in a form capable of providing the substituted cyclohexyl group as a free radical with the electron in the correct position vis-a-vis the t-alkyl substituent either spontaneously or under oxidising conditions and, if desired, hydrolysing the Y group (other than hydroxy) into a 3-hydroxy group in the resulting 2-cycloalkyl substituted condensate.

A suitable donor is the corresponding substituted cyclohexyl carboxylic acid which may undergo oxidative decarboxylation. For instance persulphate with a catalyst, such as silver ions, is convenient for the purpose (c.f. Jacobson N. et al., *Annalen,* 1972, 763, 135 and *Acta Chem. Scand,* 1973,27, 3211). Preferably, when persulphate is used under those conditions, the reaction is carried out with a 1,4-naphthoquinone in which Y is other than hydroxy. Conveniently ammonium persulphate can be used as the oxidising agent, and the catalyst is silver nitrate. Hydrolysis subsequent to the main coupling reaction may, if required, provide the hydroxy group. Alkaline conditions are usually preferred for the hydrolysis.

An example of the donor itself carrying a peroxide grouping is the method employing an appropriately substituted cycloalkanoyl peroxide as suggested by U.S. Pat. No. 2,553,647.

The provision of the cycloalkyl free radical by a spontaneous release from the donor can for instance be achieved by the use of a tricycloalkylborane. Such reagent can easily be prepared by reacting the cycloalkene with borane dimethylsulphide. Conveniently the reaction is carried out in a solvent such as tetrahydrofuran.

Also of use as a cyclohexyl donor is the corresponding substituted cyclohexenyl carboxylic acid; if used it will be clear to those skilled in the art that an additioned step of reduction of the alkene will be required following condensation to provide compounds of formula (I).

It will be appreciated by those skilled in the art that the above process will lead to a mixture of cis and trans isomers.

It has been found that the non-stereospecific preparative methods generally lead to an approximately 1:1 ratio of the cis and trans isomers. However, where desired the amount of trans isomer in the recovered product may be increased by adjustment of reaction conditions, in particular by selection of a solvent system in which the trans isomer is less soluble. Such solvent systems may be readily determined by experiment but a solvent system found to be particularly effective is a mixture of water and acetonitrile. By use of such systems cis to trans ratios of from about 2:3 to about 1:4 may be obtained.

Where a single isomer, cis or trans, is desired this may be obtained by stereospecific synthesis, as described above or by separation of the isomers by physical means. Such methods are well known in the art and include, for example, fractional crystallisation or chromatographic separation.

It has further been found that the cis isomer of compounds of formula (I) may be epimerised to the trans isomer thereof. Such epimerisation of cis to trans isomers of compounds of formula (I) provides a further aspect of the present invention.

In particular this may be achieved by treatment with certain mineral acids, in particular concentrated sulphuric acid. The degree of conversion of cis isomer to trans isomer in such epimersations may be controlled by selection of appropriate reaction conditions, in particular temperature and duration of reaction. Under appropriate conditions essentially pure trans isomer may be obtained. Suitable temperatures range from about 50° C. to about 70° C. or more and suitable reaction times from about 6 to about 24 hours or even up to 4 or 6 days or longer.

The epimerisation reactions described herein may be applied to the pure cis isomers but most conveniently will be applied to mixtures of isomers obtained by non-stereospecific synthetic methods. The reaction may be used either to provide trans isomers of compounds of formula (I) essentially free of the cis isomer or mixtures thereof containing desired ratios of cis to trans isomers, for example 5:95, 3:97 or other desired ratios.

In a yet further aspect the present invention provides compounds of formula (VIII)

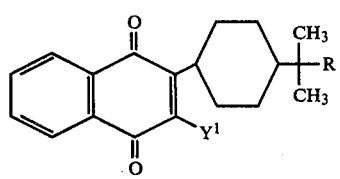

(VIII)

wherein $Y^1$ is a halogeno, acetoxy, benzoyloxy or $C_{1-6}$ alkoxy group. These are novel compounds and are useful as intermediates in the syntheses described above. Those which carry a group for $Y^1$ which is easily hydrolysed in vivo into the hydroxy group, may be used as pro-drugs in formulations or for treatment to provide the hydrolysed end-product in situ. The acetyl or benzoyl group may undergo such hydrolysis and are thus of potential as long acting precursors of active compounds.

The compounds of formula (I) have been found to be extremely active against the human malaria parasite *Plasmodium falciparum* and are thus of use in the treatment and/or prophylaxis of malaria in man. The compounds have also been found to be extremely active against protozoa causing the commercially important forms of coccidiosis, in particular *Eimeria tenella* and *E. acervulina* and are thus of use in the treatment or prophylaxis of coccidiosis in animals, particularly birds.

The compounds of formula (I) have also been found to be inhibitors of both cyclo oxygenase and lipoxygenase enzymes in rabbit polymorphonunclear leucocytes 'in vitro'. It has also been found that the compounds of formula (I) inhibit leucocyte accumulation in the aqueous humour of the inflammed rat eye following both oral and topical administration.

The compounds of formula (I) are thus of value for the treatment of medical conditions which may be alleviated by the inhibition of the lipoxygenase and cyclo oxygenase pathways of Arachidonic Acid (A.A) metabolism for example the relief of arthritic conditions, inflammatory skin (eg, eczema) and eye (eg. conjunctivitis) conditions.

It will be appreciated that the amount of compound of formula (I) required for use in treatment or prophylaxis will vary not only with the active compound but also with the route of administration and nature of the infection. In general a suitable dose for a mammal (including man) for treatment, for example of malaria, will lie in the range of 0.1 mg to 200 mg per kilogram body weight per day, with a preferred range of 1 mg to 100 mg, particularly 10 to 40 mg. For the prophylaxis or treatment of coccidiosis the compound will normally be administered ad lib in drinking water or diet and suitable levels of drug will be in the range of 1 to 500 ppm, preferably 10–400 ppm ideally about 200 ppm.

While it is possible that, for use as antiprotozoal or anti inflammatory agents, the compounds of formula (I) may be administered as the raw chemical it is preferable to present the active ingredient as a pharmaceutical or verterinary formulation.

Pharmaceutical formulations comprise the active compounds together with one or more pharmaceutically acceptable carriers therefor and optionally other therapeutic and/or prophylactic ingredients. The carrier(s) must be 'acceptable' in the sense of being compatible with the other ingredients of the formula and not deleterious to the recipient thereof.

The active compound(s) may conveniently be presented (as a pharmaceutical formulation) to unit dosage form. A convenient unit dose formulation contains the active ingredient compound(s) in an amount of from 10 mg to 1 g.

Pharmaceutical formulations include those suitable for oral, rectal or parenteral (including intramuscular and intravenous) administration, although oral is the preferred route. The formulations may, where appropriate, be conveniently presented in discrete dosage units and may be prepared by any of the methods well known in the art of pharmacy. All methods include the step of bringing into association the active compound with liquid carriers or finely divided solid carriers of both and then, if necessary, shaping the product into the desired formulation.

Pharmaceutical formulations suitable for oral administration wherein the carrier is a solid are most preferably presented as unit dose formulations such as boluses, capsules, cachets or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Moulded tablets may be made by moulding an inert liquid diluent. Tablets may be optionally coated and, if uncoated, may be optionally scored. Capsules may be prepared by filling the active compound, either alone or in admixture with one or more accessory ingredients, into the capsule cases and then sealing them in the usual manner. Cachets are analogous to capsules wherein the active ingredient together with any accessory ingredient(s) is sealed in a rice paper envelope.

Pharmaceutical formulations suitable for oral administration wherein the carrier is a liquid may be presented as a solution or a suspension in an aqueous liquid or a non-aqueous liquid, or as an oil-in-water or water-in-oil liquid emulsion.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping moulds.

Pharmaceutical formulations suitable for parenteral administration include sterile solutions or suspensions of the active compound in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The veterinary formulations of the present invention are preferably in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the active ingredient(s), and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water soluble compound of formula (I) or a salt thereof and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals particularly poultry.

The compounds of the present invention may also be used in combination with other therapeutic agents for example other antiprotozoal agents. In particular the compounds of the invention may be employed together with known antimalarial and/or anticoccidial agents.

The invention thus provides, in a further aspect, a combination comprising a compound of formula (I) as defined herein or a pharmaceutically acceptable salt thereof together with another therapeutically active agent, in particular an antimalerial or anticoccidial agent.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The combination defined above, in particular when a second antimalarial or anticoccidial agent is employed, are of value inter alia in delaying the onset of resistance to the compounds of formula (I).

Suitable therapeutic agents for use in the mixtures defined above include, for example, pyrimethamine, chloroquine, mefloquine, quinine, primaquine, monensin, halofuginone, arprinocid and zoalene.

When compounds of formula (I) used in combination with a second therapeutic agent effective against the same parasites the dose of each compound will vary from that when the compound is used alone. Appropriate doses will be readily appreciated by those skilled in the art.

EXAMPLE A

Preparation of 4-t-alkyl-cyclohexane carboxylic acids

The carboxylic acids used in the following examples were prepared as follows:
(i) 4-t-Butylcyclohexane-1-carboxylic acid, 4-t-butylcyclohexylacetic acid, and the pure cis and trans isomers thereof were either obtained commercially or as described in the literature (J.Amer.Chem.Soc. 1970, 92, 2800 and references therein).
(ii) 4-t-Pentylcyclohexyl-1-carboxylic acid (cis/trans mixture) and pure trans 4-t-pentylcyclohexyl-1-carboxylic acids were obtained as follows:

(a) Preparation of cis/trans-4-t-pentylcyclohexyl-1-carboxylic acid 4-t-pentylcyclohexane (49.2 g) was dissolved in ether (200 ml), and sodium cyanide (24.46 g) and water (30 ml) added. The mixture was cooled to 0° and stirred vigorously while concentrated hydrochloric acid was added dropwise over 1 hour. Stirring was continued for a further 3 hours and the mixture was then allowed to stand overnight. The reaction mixture was washed with saturated sodium metabisulphite (2×200 ml) and the ether layer dried over sodium sulphate. Removal of solvent in vacuo affored the cyanohydrin as a pale yellow oil, 54.0 g.

The cyanohydrin (54.0 g) was dissolved in anhydrous pyridine (70 ml) and anhydrous benzene (70 ml), stirred and cooled to 0°. Phosphoryl chloride (90 ml) in pyridine (83 ml) was added, dropwise over 45 mins., whilst the temperature was kept at 0°. The reaction mixture was allowed to warm to reflux for a further 30 mins.

The mixture was allowed to cool, poured onto ice, stirred for 30 mins., and then extracted with ether, washed with water, dried (sodium sulphate) and evaporated to dryness in vacuo to yield 4-t-pentylcyclohex-1-ene-1-nitrile, 48.4 g, as an oil. 1-4-t-Pentylcyclohex-1-ene-1-nitrile (48.0 g) was added to a mixture of potassium hydroxide (23.3 g) in water (34 ml) and ethanol (150 ml). The mixture was heated under reflux for 72 hours, cooled in ice, diluted with water (175 ml) and then acidified with concentrated hydrochloric acid. A colourless solid was precipitated filtered, washed with water, and dried (sodium sulphate). The solid was partitioned between ethyl acetate and sodium hydroxide solution (2N), the basic layer was separated and acidified with concentrated hydrochloric acid, and the resultant colourless solid collected by filtration, washed with water, and dried to give 4-t-pentylcyclohex-1-ene-1-carboxylic acid, 33.65 g, mp 123°–125°.

4-t-Pentylcyclohex-1-ene-1-carboxylic acid (33.5 g) was dissolved in ethanol (275 ml), and 10% palladium on charcoal (1.0 g), added. The mixture was hydrogenated at 10 atm until the theoretical value of hydrogen had been taken up. The catalyst was filtered off and the colourless filtrate evaporated to dryness in vacuo to give 4-t-pentylcyclohexyl-1-carboxylic acid, as an oil, 27.0 g (cis/trans mixture).

(b) Preparation of pure trans-4-t-pentylcyclohexyl-1-carboxylic acid

The cis/trans mixture of acids (12 g, prepared by method (a) above) was heated in a steam bath in the presence of concentrated sulphuric acid (60 ml) for 16 hours. The reaction mixture was cooled, poured onto ice and a blank solid formed. The solid was filtered, and dried and then triturated with light petroleum (40°–60°) until most of the solid had dissolved. The petroleum extract was treated with charcoal and then evaporated to dryness in vacuo to yield trans-1-4-t-pentylcyclohexyl-1-carboxylic acid, 5.7 g, mp 92°–100°. NMR spectroscopy showed the product to be 95–97% pure trans isomer.

The following examples illustrate the invention:

EXAMPLE 1

Preparation of 2-(4'-t-butylcyclohexyl)-3-hydroxy-1,4-naphthoquinone

A mixture of 2-chloro-1,4-naphthoquinone (21 g), 4-t-butylcyclohexane-1-carboxylic acid (19.8 g) and silver nitrate (3.6 g) was heated at 70°–75° C. with vigorous stirring in a solvent mixture of acetonitrile (30 ml), sulpholane (90 ml) and water (210 ml) whilst a solution of ammonium persulphate (34.2 g) in water (60 ml) was added dropwise during 30 minutes. Stirring and heating was continued for a further hour, the mixture cooled in ice and extracted with diethyl ether. The extracts were washed with aqueous sodium bicarbonate solution, dried and evaporated under reduced pressure to a semi-solid which was crystallised twice from acetonitrile to provide 2-(4-butylcyclohexyl)-3-chloro-1,4-naphthoquinone m.p. 107°–110°.

The so obtained chloroquinone (12.1 g) was suspended in boiling methanol (300 ml) and a solution of potassium hydroxide (12.1 g) in water (120 ml) added dropwise during 15 minutes. The mixture was refluxed for a further hour and then treated with concentrated hydrochloric acid (60 ml). The mixture was cooled on ice, the crystalline material collected and washed with water. Recrystallisation from acetonitrile gave 2-(4-t-butylcyclohexyl)-3-hydroxy-1,4-naphthoquinone m.p. 123°–126°. The material had a cis/trans ratio of approximately 1:1.

When the solvent mixture used in the first step was altered to acetonitrile/water a cis/trans ratio of final product of 2:8 was obtained (m.p. 126°–128°).

EXAMPLE 2

Preparation of 2-(trans-4'-t-butylcyclohexyl)-3-hydroxy-1,4-naphthoquinone

A mixture of 2-chloro-1,4-naphthoquinone (960 mg), 1-(trans-4-t-butylcyclohexyl)acetic acid (990 mg prepared by the method described in J. Amer. Chem. Soc. 1970, 92,2800) and silver nitrate (250 mg) in acetonitrile (9 ml) was heated to reflux with vigorous stirring whilst a solution of ammonium persulphate (3.0 g) in water (12 ml) was added dropwise over 1 hour. The mixture was refluxed for a further hour, cooled in ice and the yellow solid so obtained collected and washed with water. The solid was extracted with hot ethyl acetate which on cooling yielded 2-(trans-4'-t-butylcyclohexylmethyl)-3-chloro-1,4-naphthoquinone m.p. 154°–156°. NMR spectroscopy confirmed that the material was 100% trans isomer.

Chloroquinone (6 g) obtained as described above in dimethoxyethane (60 ml) and water (60 ml) was heated under reflux whilst potassium hydroxide (6.0 g) in water (60 ml) was added dropwise over 10 minutes. Reflux was continued for a further 15 minutes, the mixture cooled raidly to ambient temperature and acidified with concentrated hydrochloric acid. The bright yellow solid so obtained was collected, washed with water and dried to yield 2-(trans-4-t-butylcyclohexyl-methyl)-3-hydroxy-1,4-naphthoquinone m.p. 180°–182°.

The above obtained hydroxyquinone (4.36 g) was dissolved in dioxane (32 ml) and sodium carbonate (1.6 g) in water (32 ml) added with stirring. The mixture was heated to 70° C., 30% hydrogen peroxide (3.0 ml) added and heating maintained. After 30 minutes a further portion of 30% hydrogen peroxide (0.5 ml) was added and heating continued until a pale yellow solution was obtained. The mixture was then cooled in ice and treated with concentrated hydrochloric acid (3.0 ml) followed by water saturated with sulphur dioxide (20 ml), and while maintaining the temperature at 0° C., nitrogen was blown through the mixture with vigorous stirring for 2 hours. Aqueous sodium hydroxide solution (25%; 28 ml) was added followed by a solution of copper sulphate pentahydrate (13.2 g) in water (68 ml).

The mixture was heated with occasional stirring on a steam bath for 10 minutes, followed by stirring at ambient temperature for 10 minutes. The mixture was filtered and the solid washed with dioxane (2×10 ml); water (2×10 ml) and dioxane (10 ml) and the combined filtrates acidified with concentrated hydrochloric acid. The precipitate was collected, washed with water, dried and recrystallised from petroleum ether (30 ml) to give 2-(trans-4'-t-butylcyclohexyl)-3-hydroxy-1,4-naphthoquinone m.p. 134°–136° which was shown to be isomerically pure by NMR spectroscopy.

EXAMPLE 3

2-(Cis-4'-t-butylcyclohexyl)-3-hydroxy-1,4-naphthoquinone

By method of Example 2, but in which the trans carboxylic acid was replaced by the cis carboxylic acid was obtained 2-(cis-4'-t-butylcyclohexyl)-3-hydroxy-1,4-naphthoquinone, m.p. 113°–115°. shown by NMR spectroscopy to be isomerically pure.

The physical properties of the intermediates were:

2-(cis-4'-t-butylcyclohexylmethyl)-3-chloro-1,4-naphthoquinone m.p. 111°–113°.

2-(cis-4'-t-butylcyclohexylmethyl)-3-hydroxy-1,4-naphthoquinone m.p. 124°–125°.

EXAMPLE 4

2-Hydroxy-3-(4'-t-pentylcyclohexyl)-1,4-naphthoquinone

By the method of Example 1 was prepared 2-hydroxy-3-(4'-t-pentylcyclohexyl)1,4-naphthoquinone m.p. 79°–81°. The cis/trans isomer ratio was found to be 2:3 by NMR spectroscopy. The intermediate, 2-chloro-3-(4'-t-pentylcyclohexyl)-1,4-naphthoquinone, was a viscous oil.

EXAMPLE 5

Epimerisation of cis 2-(4'-t-butylcyclohexyl)-3-hydroxy-1,4-naphthoquinone

An approximately 1:1 cis/trans mixture of 2-(4'-t-butylcyclohexyl)-3-hydroxy-1,4-naphthoquine (see Example 1) (10 g) was dissolved in concentrated sulphuric acid (100 ml) and the solution maintained at various temperatures for various periods of times as shown below. At the end of the reaction the reaction mixture was cooled and poured dropwise into ice/water to provide crude product which was purified by recrystallisation as previously described and/or column chromatography. The isomers ratios of the product were determined by NMR, GLC.; the results shown below.

| Temperature °C. | Time | Isomer Ratio trans:cis |
|---|---|---|
| 50 | 4 days | 93:7 |
| 56 | 24 hr | 96.5:3.5 |
| 56 | 24 hr | 97.7:2.3 (recrystallised) |
| 70 | 4 hr | 92.0:8.0 |
| 70 | 6 hr | 97.8:2.2 |
| 70 | 6 hr | 99.2:0.8 (recrystallised) |
| 70 | 21 hr | 99.4:0.6 |
| 70 | 21 hr | 99.9:0.1 (recrystallised) |

EXAMPLE 6

Activity of 2-(substituted cyclohexyl)-3-hydroxynaphthoquinones against *Plasmodium falciparum*

Compounds of the following formula, including compounds of formula (I), were examined for their inhibitory effect on *Plasmodium falciparum*.

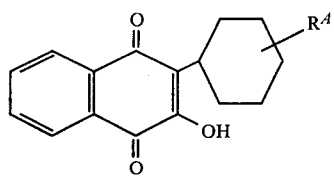

The test method was a modification of that described by Desjardins et al., Antimicrob. Agents and Chemotherapy, 1979, 16, 710–718. Compounds were dissolved in ethanol at a concentration of 1000 mg/L and dilutions down to 1 mg/L were made. The drug solutions were serially diluted using RPMI 1640 medium + 10% human plasma in microtitration plates. Parasitised and fresh red blood cells were added together with $G^3H$-hypoxanthine, in RPMI 1640 medium + 10% human plasma and the cultures incubated for 36 hours. Cultures were then harvested, the particulate contents collected on a glassfibre filter paper and washed copiously with water. The filter papers were dried and the radioactivity measured using a scintillation counter. Infected untreated and uninfected untreated cultures were included as controls. Percent inhibition was correlated with dose to provide an $ED_{50}$.

The results are shown in Table 1.

TABLE 1

| $R^A$ | $ED_{50}(M)$ |
|---|---|
| 4'-Cyclohexyl (100% trans) | $4.05 \times 10^{-9}$ |
| 4'-Methyl (100% trans) | $9.2 \times 10^{-9}$ |
| 3'-t-Butyl (80% trans) | $3.0 \times 10^{-7}$ |
| 4'-t-Butyl (50% trans) | $5.99 \times 10^{-10}$ |
| 4'-t-Butyl (75% trans) | $5.63 \times 10^{-11}$ |
| 4'-t-Butyl (80% trans) | $3.75 \times 10^{-11}$ |
| 4'-t-Butyl (100% cis) | $1.08 \times 10^{-9}$ |
| 4'-t-Butyl (100% trans) | $5.71 \times 10^{-11}$ |
| 4'-t-Pentyl (60% trans) | $6.0 \times 10^{-11}$ |

Menoctone /2-(8-cyclohexyloctyl)-3-hydroxy-1,4-naphthoquinone/ was found to have an $ED_{50}$ of $2.55 \times 10^{-7}$.

The results show that the compounds of formula (I) were significantly more active than the other compounds tested against the human parasite, *P. falciparum*.

EXAMPLE 7

Activity of 2-(substituted cyclohexyl)-3-hydroxy naphthoquinones against Eimeria species (a) In vitro activity against *E. tenella*

Compounds tested in Example 5 were assessed for their activity against *E. tenella*. In the method employed cell cultures were infected with sporozoite suspensions of *E. tenella* immediately after addition of the compounds. Serial dilutions of solutions of the compounds were made as in Example 6 in a range of concentration of 19 ug/l to 20 mg/l in order to determine the minimum inhibitory concentration (MIC). After incubation for 96 hours the cultures were fixed and the cells were stained with 0.1% toluidine blue. The stained cultures were examined microscopically for presence of parasites. The results obtained are shown in Table 2.

TABLE 2

| $R^A$ | MIC(M) |
|---|---|
| 4'-Cyclohexyl (100% trans) | $9.2 \times 10^{-8}$ |
| 4'-Methyl (100% trans) | $4.6 \times 10^{-7}$ |
| 3'-t-Butyl (80% trans) | $4.0 \times 10^{-6}$ |

TABLE 2-continued

| $R^A$ | MIC(M) |
|---|---|
| 4'-t-Butyl (80% trans) | $1.0 \times 10^{-8}$ |
| 4'-t-Butyl (100% trans) | $2.5-4.0 \times 10^{-9}$ |
| 4'-t-Butyl (100% cis) | $2.5 \times 10^{-8}$ |
| 4'-t-Pentyl (50% trans) | $9.6 \times 10^{-9}$ |
| 4'-t-Pentyl (60% trans) | $9.6 \times 10^{-9}$ |
| 4'-t-Pentyl (96% trans) | $9.6 \times 10^{-9}$ |

(b) In vivo activity against *E. tenella* and *E. acervulina*

Compounds tested in Example 7(a) were examined in an in vivo anticoccidiosis screen.

The compounds were administered to groups of 5 male Ross Ranger chicks (7 days old), at various dosages in the diet, for 6 days. The chicks were each infected with *Eimeria tenella* and *E. acervulina* one day after the beginning of the medication. The number of birds cleared of *E. tenella* lesions was noted on the fifth day of infection as was the presence or absence of *E. acervulina* oocysts in the droppings. The results are shown in Table 3, in which the numbers refer to the number of birds cleared of *E. tenella* and the letters indicate the presence or absence of *E. acervulina* /A=absent; P=present; M=95% clearance in comparision with untreated controls/.

TABLE 3

| | Dosage (ppm) | | |
|---|---|---|---|
| $R^A$ | 50 | 100 | 200 |
| 4'-Cyclohexyl (100% trans) | 1/5 (P) | 5/5 (P) | 5/5 (A) |
| 4'-t-Butyl (80% trans) | 0/5 (P) | 5/5 (A) | NOT TESTED |
| 4'-t-Pentyl (60% trans) | 4/5 (M) | 5/5 (A) | 5/5 (A) |

EXAMPLE 8

Toxicity

The acute oral $LD_{50}$'s of compounds of formula (I) in rats were determined by standard techniques. The results are shown below.

| Compound | $LD_{50}$ |
|---|---|
| 2-(4'-t-butylcyclohexyl)-3-hydroxy-1,4-naphthoquinone | >1000 mg/kg bodyweight |
| 2-hydroxy-3-(4'-t-pentylcyclohexyl)-1,4-naphthoquinone | 2000 mg/kg bodyweight |

EXAMPLE 9

Formulations

| Tablet formulation | |
|---|---|
| Compound of formula 1 | 100 mg |
| Lactose | 100 mg |
| Maize starch | 30 mg |
| Magnesium stearate | 2 mg |
| | 232 mg |
| Oral suspension | |
| Compound of formula 1 | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |
| Injectable suspension | |
| Compound of formula 1 | 100 mg |
| Polyvinyl pyrrolidine (RVP) | 170 mg |
| Tween 80 | 0.2% v/v |
| Methylhydroxybenzoate | 0.1% w/v |
| Water for injection | to 3 ml |
| Capsule | |
| Compound of formula 1 | 100 mg |
| Starch 1500 | 150 mg |
| Magnesium stearate | 2.5 mg |
| filled into a soft gelatin capsule | 2.5 mg |

EXAMPLE 10

Anti-inflammatory activity (a) In vitro activity

In an eczyme assay according to the method of G. Blackwell and R. J. Flower (Br.J.Pharmac. 63: 360P (1978)) compounds of formula (I) were found to have an $IC_{50}$(uM) for inhibition of each of lipoxygenase and cyclo oxygenase as indicated below.

| | $IC_{50}$ (uM) | |
|---|---|---|
| Compound of formula (I) | Cyclo oxygenase | Lipoxygenase |
| R = $CH_3$ | 58 | 23 |
| R = Et | 63 | 29 |

(b) In vivo activity

The anti-inflammatory activity in the rat eye was determined, following both oral and topical administration, of 2-(4-t-butylcyclohexyl)-3-hydroxy-1,4-naphthoquinone. The inflammatory response for the test employed developed following injection of gram-negative bacterial endotoxin into the rat foodpad (Rosenbaum et. al Nature 286, 611–613 (1980)).

Vasodilation was assessed at 24 and 48 hours using a slit lamp, the rats then killed and the aqueous humour aspirated for determination of protein concentrations and total leucocyte numbers. The results are shown below as $ED_{50}$.

| Mode of Administration | $ED_{50}$ |
|---|---|
| Oral | 5–25 mg/kg body weight |
| Topical | 10–20 ug/eye |

We claim:

1. A compound of the formula (I)

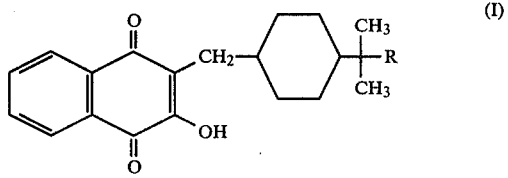

wherein R is a $C_1$–$C_{10}$ alkyl group, and pharmaceutically acceptable salts thereof.

2. A compound according to claim 1 wherein R is a straight chain alkyl group.

3. A compound according to claim 1 wherein R is a straight chain $C_{1-4}$ alkyl group.

4. A compound according to claim 1 wherein R is ethyl.

5. A compound according to claim 1 in the form of a mixture of cis and trans isomers.

6. A compound according to claim 5 wherein the ratio of cis to trans isomers is about 1:1.

7. A compound according to claim 1 in the form of the trans isomer.

8. A compound according to claim 1 in the form of the cis isomer.

9. A pharmaceutical formulation comprising a non-toxic, antiprotozoal effective amount of a compound of formula (I), as defined in claim 1 together with a pharmaceutically acceptable carrier therefor.

10. A veterinary formulation comprising a non-toxic, antiprotozoal effective amount of a compound of formula (I), as defined in claim 1, together with a veterinarily acceptable carrier therefor.

11. A method for the treatment of a protozoal infection in an animal, including man, comprising administration of an antiprotozoal effective, non-toxic amount of a compound of formula (I) as defined in claim 1.

12. A method according to claim 11 wherein the animal is a mammal and the protozoal infection is a malarial infection.

13. A method according to claim 11 wherein the animal is a bird and the infection is a coccidial infection.

14. A pharmaceutical or veterinary formulation comprising an effective combination to treat or prevent a protozoan infection comprising an effective amount of the compound of claim 1 and another antiprotozoan therapeutic agent compatible with the compound of claim 1 together with a pharmaceutically or veterinarily acceptable carrier therefor.

15. 2-(4'-tert-butylcyclohexyl)-3-hydroxy-1,4-naphthoquinone.

16. The trans isomer of 2-(4'-tert-butylcyclohexyl)-3-hydroxy-1,4-naphthoquinone.

17. The cis isomer of 2-(4'-tert-buthlcyclohexyl)-3-hydroxy-1,4-naphthoquinone.

18. A pharmaceutical composition comprising an effective anti-protozoan amount of 2-(4'-tert-butylcyclohexyl)-3-hydroxy-1,4-naphthoquinone and a non-toxic carrier therefor.

19. The method of treating or preventing malaria in a human in need thereof comprising administering an effective amount of 2-(4'-tert-butylcyclohexyl)-3-hydroxy-1,4-naphthoquinone to said human.

20. The method of treating or preventing coccidiosis in birds in need thereof which comprises administering an effective amount of 2-(4'-tert-butylcyclohexyl)-3-hydroxy-1,4-naphthoquinone to said bird.

21. The method of inhibiting the lipoxygenase and cyclooxygenase pathways of Arachidonic acid metabolism in a mammal comprising administering an effective inhibition amount of the compound of claim 1 to said mammal.

* * * * *